United States Patent [19]

Osypka

[11] Patent Number: 5,003,990

[45] Date of Patent: Apr. 2, 1991

[54] APPARATUS FOR IMPLANTING ELECTRODES AND THE LIKE IN ANIMAL BODIES

[76] Inventor: Peter Osypka, Basler Str. 109, D-7889 Grenzach-Wyhlen, Fed. Rep. of Germany

[21] Appl. No.: 387,515

[22] Filed: Jul. 28, 1989

[30] Foreign Application Priority Data

Jul. 28, 1988 [DE] Fed. Rep. of Germany ........ 3825631

[51] Int. Cl.⁵ .................. A61M 25/01; A61M 1/05
[52] U.S. Cl. ........................... 128/772; 128/785; 604/280
[58] Field of Search .............. 128/772, 784–786, 128/419 P; 604/270, 280

[56] References Cited

U.S. PATENT DOCUMENTS

| | | | |
|---|---|---|---|
| 4,057,067 | 11/1977 | Lajos | 128/785 |
| 4,289,144 | 9/1981 | Gilman | 128/785 |
| 4,402,329 | 9/1983 | Williams | 128/785 |
| 4,497,326 | 2/1985 | Curry | 128/785 |
| 4,824,435 | 4/1989 | Giesy et al. | 604/280 X |

FOREIGN PATENT DOCUMENTS

591963 7/1925 France .................. 604/270

Primary Examiner—Lee S. Cohen
Attorney, Agent, or Firm—Peter K. Kontler

[57] ABSTRACT

Apparatus for implanting surgical electrodes or catheters into human hearts or other hollow body organs has one or more flexible guide wires defining one or more tracks for a streamlined carriage the rear end of which is formed with a cavity for reception of the leading end of a catheter or electrode. The carriage can be pushed along the guide wire or wires by the electrode or catheter, and the leading end of thus implanted object is thereupon extracted from or expelled laterally from or beyond the cavity in the carriage while the carriage is held against forward and/or rearward movement with reference to the guide wire or wires. The carriage can be extracted from the body by the guide wire or wires or by means of a cord or hose. The carriage serves as a shield in front of the leading end of an electrode or catheter during introduction of the latter by way of an artery, a vein or another body cavity.

49 Claims, 6 Drawing Sheets

APPARATUS FOR IMPLANTING ELECTRODES AND THE LIKE IN ANIMAL BODIES

BACKGROUND OF THE INVENTION

The invention relates to apparatus for implanting mandrils, catheters or other elongated slender objects into the cavities of animal bodies, for example, into human hearts. More particularly, the invention relates to improvements in apparatus for arterial or interavenous implantation or for implantation by way of other body cavities. Still more particularly, the invention relates to improvements in apparatus which employ flexible guide wires.

A drawback of presently known implanting apparatus which employ guide wires is that they present problems when the path for implantation is irregular, e.g., if a vein or artery exhibits one or more pronounced curvatures, especially if the path is narrow or very narrow. If the guide wire or the leading end of the object to be implanted is pointed, it is likely to penetrate into and to injure the tissue on its way toward the ultimate destination. For example, the leading ends of many surgical electrodes constitute or include helices with sharp tips. Therefore, certain presently known electrodes include hollow sheaths into which the helical leading ends are retracted during introduction through a vein or another body cavity. Such electrodes must be equipped with complex and expensive mechanisms for expulsion or propulsion of retracted leading ends prior to anchoring in a selected portion of the body cavity, e.g., in a portion of a human heart. Moreover, the retracted leading end of a conventional electrode of the just outlined character is likely to be stiff or practically stiff which renders it difficult or impossible to introduce such electrode into and through an artery or vein.

Many arteries or veins are anatomically configurated, or are distorted (particularly narrowed) as a result of a disease, in such a way that they are practically or totally impassable to a conventional electrode, catheter or mandrin, especially if the leading end of the object to be implanted is relatively stiff. In fact, the resistance to penetration can be so pronounced that an attempt to introduce an electrode or a catheter can entail injury to the tissue and/or damage to or even total destruction of the object which is to be implanted.

Presently known guide wires are designed to extend through openings in the objects to be implanted. This contributes to the bulk, cost and rigidity of the objects and renders it even more difficult to implant the objects through narrow arteries or veins.

German Pat. No. 34 42 736 to Bonzel discloses an expansible catheter including a balloon having an inner shell which is slidable along a guide wire and an outer shell. The space between the two shells can receive a fluid.

German Pat. No. 30 10 743 to Witzel et al. discloses a similar balloon with inner and outer shells which forms part of an apparatus for the treatment of esophagus. The balloon surrounds and is movable along a gastroscope.

German published patent application No. 1 491 697 of Edwards discloses a flexible catheter with a bowden wire and a guide wire.

OBJECTS OF THE INVENTION

An object of the invention is to provide a novel and improved apparatus which renders it possible to advance the leading end of a surgical electrode or a catheter, or a medicine-containing capsule, into a selected portion of an animal body, e.g., into a selected portion of a human heart.

Another object of the invention is to provide an apparatus which renders it possible to implant an electrode with a sharp helical leading end without risking injury to the tissue during implantation.

A further object of the invention is to provide the apparatus with novel and improved means for transporting medicine of the leading end of an electrode, a catheter or a mandrin into an animal body.

An additional object of the invention is to provide an apparatus which renders it possible to introduce medicaments or elongated slender objects through veins, arteries or other body cavities.

Still another object of the invention is to provide novel and improved means for separating, or for facilitating separation of, the leading end of an electrode or a catheter from the vehicle which is used to introduce such leading end into an animal body.

A further object of the invention is to provide a simple, compact and inexpensive apparatus which can be used as a superior substitute for heretofore known implanting apparatus.

An additional object of the invention is to provide the apparatus with novel and improved means for extracting the transporting device for the leading end of a catheter or electrode from an animal body.

A further object of the invention is to provide the apparatus with novel and improved means for maintaining the helical leading end of an electrode or a mandrin out of contact with tissue during implantation of such objects into a human body.

An additional object of the invention is to provide a novel and improved method of implanting mandrins, surgical electrodes and/or catheters in a circulatory system, in a human heart or in another hollow organ of an animal body.

Another object of the invention is to provide a novel and improved method of delivering accurately metered quantities of medicaments into a human heart.

A further object of the invention is to provide a method which renders it possible to complete the implantation of electrodes, mandrins or catheters within a small fraction of the time which is needed to complete such operations in accordance with heretofore known proposals.

SUMMARY OF THE INVENTION

The invention resides in the provision of an apparatus for arterial or intravenous implantation of surgical electrodes, catheters and similar slender elongated objects of the type having helically or otherwise configurated leading ends into the circulatory system or into another cavity of an animal body, especially a human body. The improved apparatus comprises at least one elongated flexible guide wire having a proximal end and a distal end, and a discrete carriage which is guided by and is movable along the at least one guide wire (hereinafter called wire) toward and away from the distal end. The carriage has coupling means for releasably holding the leading end of a selected slender elongated object so that the leading end which is held by or in the coupling means shares the movement of the carriage toward the distal end of the wire. The coupling means can include a cavity (such as a blind hole, a through hole or an open-ended channel) in the carriage, and the latter is further provided with an open-ended channel for the wire. A blind hole can be provided in the carriage if the selected object has a helical leading end which need not be advanced beyond the carriage. The dimensions of the open-ended channel for the wire are or can be selected in such a way that the (for example, substantially spherical) distal end of the wire cannot penetrate into that end of the channel which is nearer to the distal end.

The apparatus can further comprise means for moving the carriage along the wire, especially for moving the carriage in a direction away from the distal end. The moving means can include a pull cord one end of which is separably or otherwise secured to or anchored in the carriage, preferably in that (rear) end of the carriage which faces away from the distal end of the wire.

At least a portion of the carriage (which can resemble a torpedo or an analogous streamlined body) can taper in a direction from the rear end toward the front end. The coupling means is preferably provided in the region of the rear end of the carriage The rear end of the carriage can be profiled; for example, such rear end can taper in a direction away from the front end, it can be rounded or it can have one or more facets making oblique angles with the axis of the open-ended channel for the wire.

The cavity of the coupling means can be substantially or exactly parallel to the channel for the wire. If the cavity is an open-ended hole, the helical or otherwise configured leading end of a selected object can be caused to penetrate through and beyond the open-ended hole, for example, to penetrate into and to be anchored in the tissue of the body into which the object is being implanted. The hole can be tapped so that the helical leading end of an object can be caused to advance beyond the hole by rotating the object with reference to the carriage. The carriage can be provided with means for clamping the leading end of a selected object in the cavity (e.g., in an open-ended hole) of the carriage.

If the object to be implanted is a tubular object, such as a catheter, the cavity in the carriage can constitute a hole which has an open rear end at the rear end of the carriage and includes a smaller-diameter front portion and a larger-diameter rear portion. The leading end of the tubular object fits into the larger-diameter portion of the hole and abuts a shoulder between the larger-diameter and smaller-diameter portions. In this manner, the tubular object can be used to push the carriage along the wire toward the distal end and the leading end does not directly contact the tissue adjacent the artery, vein or a body cavity which receives the object.

The channel and the hole of the carriage can be bounded by circumferentially complete internal surfaces of the carriage, and each thereof can have a circular or substantially circular cross-sectional outline.

The coupling means can include a second open-ended channel which can constitute the aforementioned through (open-ended) hole of the carriage and which can have the same cross-sectional configuration and the same dimensions as the channel for the wire. This renders it possible to mount the carriage in two different positions, namely so that the wire extends through the one or the other channel.

The carriage can be made of a plastic material which is tolerated by the animal body, and the external finish of the carriage is such that it can slide in a selected artery, vein or other cavity with a minimum of friction.

It is also possible to make the carriage from a metallic material (such as a high-quality steel) which is tolerated by a human body. A layer of inert plastic material can be provided to surround the open-ended channel for the wire, for example, if the carriage is otherwise made from a metallic material.

The apparatus can further comprise means for preventing rotation of the carriage around the wire. Such rotation preventing means can include a second guide wire, i.e., the carriage can be provided with two open-ended channels, one for each wire, and such channels are or can be at least substantially parallel to each other. The cavity of the coupling means in such carriage is spaced apart from the two channels.

The coupling means of the improved apparatus can be designed to releasably hold the leading end of a selected object with a first force, and the apparatus can further comprise means for attaching the carriage to a selected portion of the wire with a greater second force. This ensures that, when the carriage is attached to the wire, the leading end of a selected object can be separated from the coupling means (for example, it can be extracted from a cavity in the form of a hole) in response to exertion upon the selected object of a pull which exceeds the first force. The attaching means can be provided on the carriage and/or on the wire. Such attaching means can comprise a first stop on the wire and a second stop on the carriage. The stops can be designed in such a way that the second stop can ride over the first stop in a direction toward the distal end of the wire but cannot move beyond the second stop in the opposite direction. The first and second stops can be said to constitute complementary first and second detent elements which cooperate to attach the carriage to the wire in a selected position (e.g., at a selected distance from the distal end of the wire) or in such a way that the carriage can move toward but cannot move away from the distal end.

In accordance with a modification of the attaching means, the second detent element can comprise a socket in the distal end of the wire and the first detent element can comprise a projection which is provided on the carriage and is arranged to snap or otherwise enter into the socket when the carriage is advanced to a position at a predetermined distance from the distal end.

At least one of the detent elements can be made of a plastic material.

The means for preventing movements of the carriage in a direction away from the distal end of the wire can comprise a tubular stop which is slipped onto the wire behind the carriage so that its front end face abuts or is affixed to the rear end of the carriage. Such stop can be used to push the carriage toward the distal end of the wire in addition to or in lieu of an elongated object the leading end of which is engaged by the coupling means. The length of the tubular stop with reference to the wire can be selected in such a way that the stop can hold the carriage against movement away from the distal end of the wire when the carriage reaches a position at a selected distance from the distal end.

The second detent element can include or constitute a recess which is provided in the wire, e.g., adjacent its distal end. The first detent element of such attaching means can constitute an elastic male detent element (e.g. a leaf spring) which abuts the wire while the carriage advances toward the recess and which is free to snap into the recess when the carriage reaches a position at a selected distance from the distal end of the wire. The elastic detent element then cooperates with the wire to prevent the carriage from moving in a direction away from the distal end of the wire. The elastic detent element can be installed in the carriage adjacent the channel for the wire so that it tends to penetrate into the channel but is held against such penetration by the wire until the channel comes to a position of register with the recess in the wire.

A portion of the elastic detent element can be configurated and dimensioned in such a way that it engages and holds the helical or otherwise configurated leading end of a selected object in the cavity of the coupling means until the elastic detent element is free to enter the recess of the wire. Thus, the elastic detent element is automatically detached from the leading end in the cavity of the carriage when it is free to cooperate with the wire in order to attach the carriage to the wire. The aforementioned portion of the elastic detent element can extend between two neighboring helices of the leading end in the cavity of the coupling means. Instead of penetrating between two helices of a leading end, the aforementioned portion of the elastic detent element can extend into a suitable socket of the leading end in the cavity, e.g., into a radial hole in the front end portion of a tubular object such as a catheter.

The carriage can be provided with a suitably inclined ramp in front of the cavity of the coupling means, and with a lateral outlet for the leading end of an object. This renders it possible to expel the leading end from the cavity by urging the object forwardly so that the leading end of the object slides along the ramp and leaves the carriage by way of the lateral outlet. Such outlet preferably extends in a direction away from the open-ended channel for the wire. At least one constriction can be provided at the inlet of the cavity and/or adjacent the outlet, especially if the leading end of an object to be implanted is a helix. At least a portion of such constriction can penetrate between the helices of the leading end in the cavity. The constriction can further define a passage which communicates with and widens toward the outlet but is too narrow to permit escape of the leading end.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain presently preferred specific embodiments with reference to the accompanying drawing.

DESCRIPTION OF PREFERRED EMBODIMENTS

Figure 1:
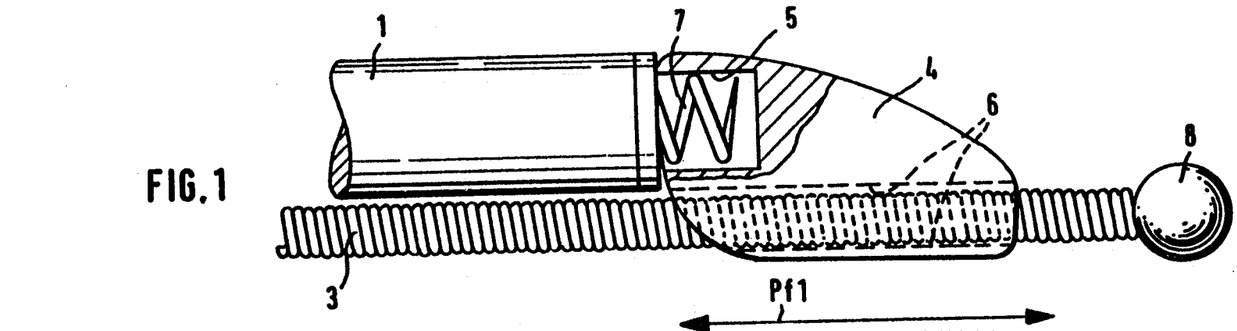
FIG. 1 is an enlarged fragmentary schematic elevational view of an apparatus which embodies one form of the invention and wherein the helically configurated leading end of an electrode is received and held in a cavity at the rear end of a discrete carriage which is reciprocable along a single guide wire and is shown adjacent the distal end of the guide wire.

The apparatus which is shown in the drawing serves for intravenous or arterial implantation of surgical electrodes 1, catheters 2 or other elongated slender objects into the cavities of animal bodies, e.g., into a human heart The apparatus comprises an elongated flexible guide wire 3 which has a proximal end (not shown) and a distal end 8. FIG. 1 shows a distal end 8 which constitutes or resembles a sphere having a diameter such that it cannot penetrate into the open front end of an elongated straight channel 6 in a streamlined discrete carriage or slide 4 which is reciprocable along the wire 3 in directions indicated by double-headed arrow Pf1. The guide wire 3 is flexible and comprises a plurality of closely adjacent convolutions to impart to the wire a required flexibility for introduction into a human heart or into another part of an animal body.

The carriage 4 is readily slidable along the wire 3 in directions toward and away from the distal end 8, and its rear end (namely the left-hand end as seen in FIG. 1) includes coupling means here shown as including a cavity in the form of a blind hole 5. This hole is parallel to the channel 6 and receives and retains the helical leading end 7 of a surgical electrode 1 which is to be introduced into an animal body with assistance from the carriage 4 and wire 3. The carriage 4 not only serves as a vehicle for transporting the leading end 7 to a selected location but also as a means for preventing the helical leading end 7 from engaging the tissue ahead of the intended locus of such leading end when the implantation of the electrode 1 is completed. In lieu of an electrode 1 or a catheter 2 (FIG. 4), the improved apparatus can be used with equal or similar advantage for the implantation of mandrins or other elongated slender objects which are used in conjunction with cardiac pacemakers or for other purposes. Still further, a mandrin can be used in lieu of the electrode 1 or catheter 2 in order to push the carriage 4 to a selected position where the carriage dispenses a medicine in a selected portion of a body cavity.

The carriage 4 of FIG. 1 has a single elongated open-ended channel 6 because it is guided by a single wire 3. The distal end 8 of the wire 3 determines the extent of penetration of the carriage 4 into an animal body because such distal end cannot enter the channel 6. Moreover, the wire 3 can be used as a means for extracting the carriage 4 from a body, for example, after the leading end 7 of the electrode 1 is detached from the carriage (i.e., withdrawn from the blind hole 5) and anchored in a selected portion of tissue adjacent the body cavity which has received the wire 3 and the carriage 4.

Figure 3:
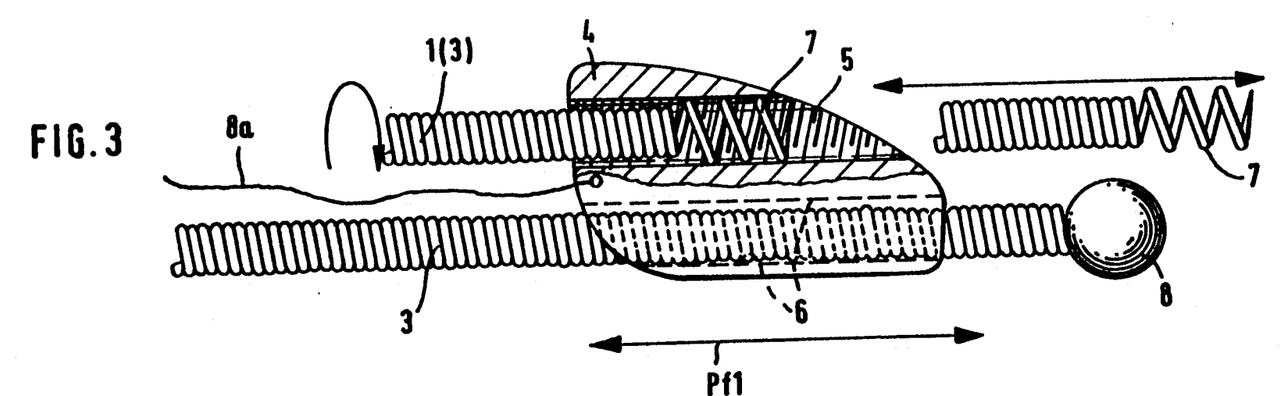
FIG. 3 is a fragmentary elevational view of a third apparatus which has means for moving the carriage along the guide wire and wherein the coupling means includes a through hole in the carriage.

If the carriage 4 is to be extracted from a body cavity without the wire 3, the apparatus can be provided with means for moving the carriage away from the distal end 8 of the inserted wire. This is shown in FIG. 3 where the moving means comprises a flexible cord 8a the front end portion of which is separably affixed to or anchored in the rear end of the carriage and can be pulled in a direction to the left to draw the carriage away from the distal end 8 of the wire 3. The moving means can include two or more cords 8a or the like. This apparatus will be put to use when it is desired to leave the wire 3 in the body cavity but to move one and the same carriage 4 back and forth along the wire 3 or to use several discrete carriages as vehicles for implantation of electrodes, catheters or other elongated slender objects or as vehicles for delivery or evacuation of medicaments.

The carriage 4 preferably tapers in a direction from its rear end toward its front end, and its front end (facing the distal end 8 of the wire 3) is preferably rounded, the same as the rear end. Instead of or in addition to being rounded, the rear end of the carriage 4 can be profiled in a different way, e.g., it can simply taper in a direction away from the front end and/or it can be provided with one or more facets which make oblique angles with the axis of the channel 6. As can be seen, for example, in FIG. 1, a portion of the rear end of the carriage 4 is rounded in the region of the open rear end of the channel 6, and such rounded portion merges into a facet which is inclined with reference to the axis of the channel 6. When considered as a whole, the rear end of the carriage 4 tapers in a direction away from the front end, i.e., in a direction away from the distal end 8 of the wire 3. The just described configuration of the rear end of the carriage 4 facilitates its movement in a direction away from the distal end 8.

The blind hole 5 which constitutes the cavity of the carriage 4 shown in FIG. 1 is or can be substantially parallel to the channel 6. This reduces the likelihood of tilting and jamming of the carriage 4 with reference to the wire 3 while the electrode 1 is being pushed to the right in order to advance the carriage toward the distal end 8 of the wire 3.

Figure 2:
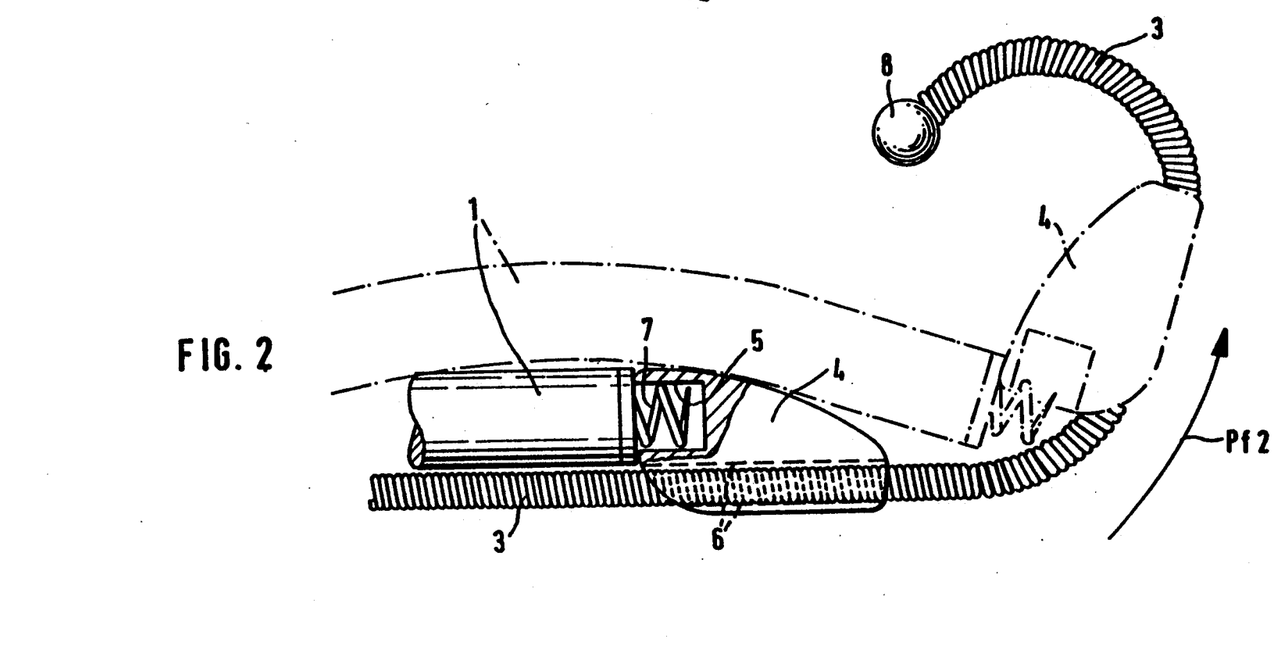
FIG. 2 is a similar fragmentary elevational view of a second apparatus with a specially designed guide wire and with a carriage which brings about automatic separation of the leading end of an electrode when the carriage approaches the distal end of the guide wire.

FIG. 2 shows one presently preferred mode of ensuring predictable separation of a properly implanted object (such as a surgical electrode 1) from the carriage 4. To this end, the front portion of the wire 3 (immediately or closely behind the distal end 8) is curved so that it resembles the letter C or J. As the carriage 4 advances from the solid-line position toward the broken-line position of FIG. 2 (note the arrow Pf2), its inclination with reference to the leading end 7 of the electrode 1 changes, the same as the inclination of the axis of the blind hole 5 in the rear end of the carriage. This entails automatic separation of the leading end 7 from the carriage 4 so that the leading end can be pushed toward and anchored in a selected part of the animal body. The C-shaped or J-shaped portion of the wire 3 straightens out automatically during extraction of the carriage 4, i.e., when the distal end 8 bears against the front end of the carriage and is caused to move counter to the direction of arrow Pf2. The apparatus of FIG. 2 can be used with advantage for implantation of electrodes in the human heart; it enables the surgeon to accurately locate the helical leading end 7 in cardiac tissue subsequent to automatic separation of the leading end from the coupling means including the blind hole 5 in the rear end of the carriage 4. The means for pushing the carriage 4 toward the distal end 8 of the wire 3 is the electrode 1. An intermediate position of the electrode 1, just prior to complete separation of the leading end 7 from the carriage 4, is shown in FIG. 2 by broken lines.

The apparatus of FIG. 2 can be operated in the aforedescribed manner or in the following way: In the first step, the guide wire 3 is inserted into an artery, into a vein or into another body cavity without a carriage thereon. In the next step, the carriage 4 or an analogous carriage is slipped onto the proximal end of the inserted wire 3 and the electrode 1 or a second guide wire (with a helical leading end in lieu of a spherical distal end) is used to push the carriage 4 along the guide wire 3 and toward the broken-line position of FIG. 2. The electrode 1 or the second guide wire is automatically detached from the carriage 4 when the latter reaches the broken-line position of FIG. 2, and the guide wire 3 and its distal end 8 are then used to extract the carriage 4 from the body. The leading end 7 of the illustrated electrode 1, or the leading end of the guide wire which is used in lieu of the electrode 1 of FIG. 2, is then anchored in the tissue at a desired location in the cavity. The thus anchored electrode or guide wire can be used as a track for introduction of a carriage. The carriage which is caused to slide along the properly anchored electrode 1 or a properly anchored guide wire (which is employed in lieu of such electrode) can be used for introduction of a large-diameter catheter, such as the catheter 2 of FIG. 4.

FIG. 3 shows a portion of an apparatus wherein the coupling means of the carriage 4 includes a through hole 5 which is parallel to the channel 6 for the wire 8. The hole 5 is tapped so that it enables the helical leading end 7 of an object 1 or 3 to advance through and beyond the hole 5 in response to rotation of the object in a direction to advance the leading end 7 to the right, as seen in FIG. 3. The object which is provided with the leading 7 of FIG. 3 is a flexible wire-like electrode 1 or a guide wire 3. The diameter of the object 1 or 3 behind the leading end 7 is smaller than the inner diameter of the hole 5 so that the carriage 4 can be readily retracted as soon as the helical leading end has advanced beyond the hole 5. The carriage 4 can be retracted by the distal end 8 of the wire 3 in the channel 6 and/or by the aforediscussed cord 8a. The leading end 7 is properly anchored in the carriage 4 as long as it extends into the hole 5 and as long as the object which is provided with such distal end is not rotated about its own axis. The internal thread of the carriage 4 in the hole 5 can be said to constitute a means for releasably clamping the leading end 7 to the carriage. The surface bounding the hole 5 serves to guide the carriage 4 (together with the surface around the channel 6) while the carriage is being pulled out of the body, either by the distal end 8 or by the cord 8a.

The cord 8a constitutes an optional but highly advantageous and desirable feature of the improved implanting apparatus. Thus, this cord can be used as a convenient means for extracting the carriage 4 while the guide wire 3 remains implanted in the body. Secondly, the cord 8a can be used was a means for limiting the extent of introduction of the carriage 4 into a body. For example, the overall length or the effective length of the cord 8a can be selected in such a way that this cord causes stoppage of the carriage 4 at a preselected distance from the distal end 8 of the guide wire 3. This, in turn, renders it possible to reduce the dimensions of the distal end 8 because it is no longer necessary to ensure that the distal end 8 cannot penetrate into the channel 6 of the carriage 4. At any rate, the cord 8a enhances the reliability and the versatility of the improved apparatus.

Figure 4:
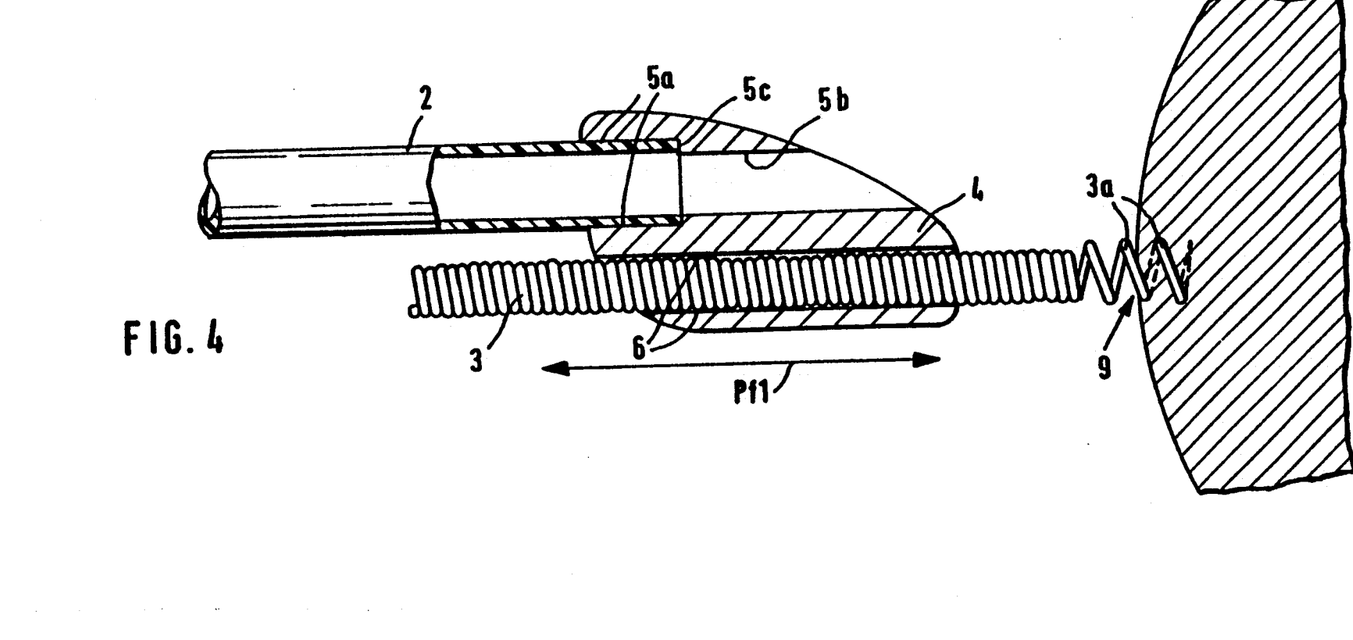
FIG. 4 is a fragmentary elevational view of a fourth apparatus with a modified guide wire which can be used as an electrode and with means for separably coupling the carriage to the leading end of a catheter.

The apparatus of FIG. 4 employs a modified wire 3 having a helical distal end 3a which can penetrate into a tissue at a selected locus 9 in an animal body. The coupling means of the carriage 4 has a through hole which is open at least at the rear of the carriage and includes a smaller-diameter portion 5b nearer to the front end of the carriage and a larger-diameter portion 5a at the rear end of the carriage. The portions 5a, 5b define an annular shoulder or stop 5c for the front end face of a catheter 2 or an analogous tubular object which is to be introduced into the animal body. The distal end 3a of the wire 3 is or can be anchored the tissue at 9 before the carriage 4 is advanced to a selected position by pushing it along the wire 3 with the catheter 2. The inserted catheter 2 can establish a path for introduction of one or more electrodes, for admission of medications and/or for other purposes. The front end of the catheter 2 can be withdrawn from the hole 5a-5b prior to extraction of the carriage 4 (e.g., by a cord, not shown in FIG. 4), and the catheter can remain implanted in the body for introduction of one or more electrodes or the like subsequent to extraction of the carriage.

The diameter of the portion 5b of the hole which is shown in FIG. 4 can match the diameter of the channel 6. This preferably also applies for the diameters of the hole 5 and channel 6 in the apparatus of FIG. 3. Such design of the carriage 4 renders it possible to slip the carriage onto a guide wire which extends through the hole (5 of FIG. 3 or 5a-5b of FIG. 4) or through the channel 6.

The carriage 4 can be made of a material (e.g., a plastic material) which can be finished to ensure that the carriage encounters little resistance to sliding movement along the guide wire 3 and/or in an artery, vein or another body cavity. It is also possible to make the carriage 4 (at least in part) from a suitable metallic material which is not likely to be rejected by the animal body. For example, the carriage 4 can be made of a high-quality steel of the type commonly used for the making of objects to be implanted in human or other animal bodies. An advantage of a metallic carriage 4 is that its movements in the interior of an animal body can be readily followed on the screen of an X-ray machine.

If desired or necessary, the surface bounding the channel 6 in a metallic carriage 4 can be coated with a layer of suitable inert plastic material. The same applies for the surface bounding the cavity (blind hole or through hole) of the carriage. The plastic material is or can be selected in such a way that it enhances the ability of the carriage 4 to slide along the guide wire or guide wires with a minimum of friction. Coating of the hole in a metallic carriage 4 with a suitable plastic material which reduces friction is often desirable and advantageous because this ensures that the leading end of an object to be implanted can be radially removed from the cavity (by moving it forwardly as in FIG. 3 or rearwardly as in FIG. 1, 2 or 4).

Figure 5:
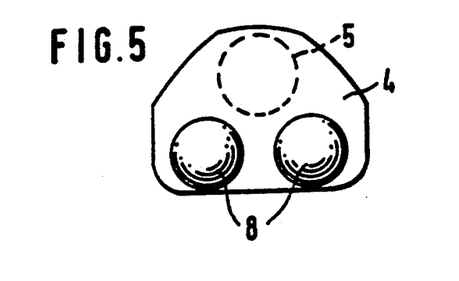
FIG. 5 is a front elevational view of a modified carriage with two channels for guide wires.
Figure 6:
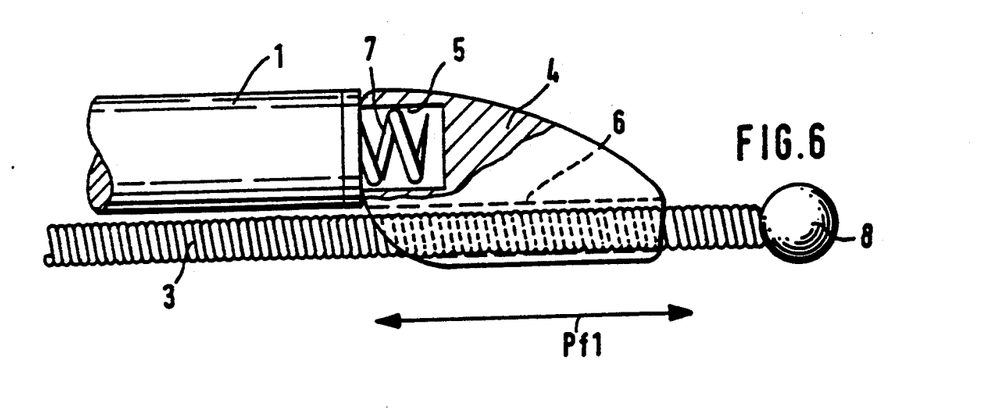
FIG. 6 is a fragmentary elevational view of an apparatus which utilizes the carriage of FIG. 5.
Figure 7:
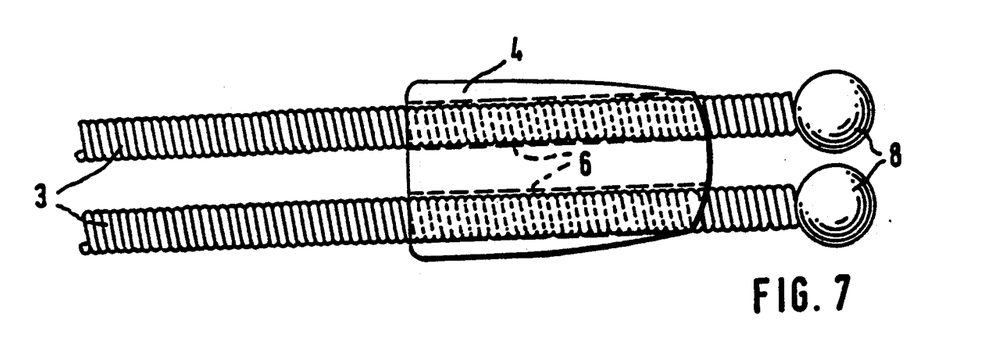
FIG. 7 is a plan view of the structure which is shown in FIG. 6.

If the carriage 4 has a blind hole 5 which is a tapped hole for reception of a helical leading end 7, such leading end can be readily extracted from the blind hole by rotating the respective object with reference to the carriage. This is possible if the object can be readily rotated with reference to the carriage 4, i.e., if the carriage cannot share the rotary movement of the object in a direction to withdraw the helical leading end 7 from a tapped hole of the carriage. FIGS. 5 to 7 show one mode of preventing rotation of the carriage 4 with the leading end 7 of an electrode 1. The carriage 4 has two parallel open-ended channels 6 and the apparatus comprises two flexible guide wires 3 having spherical distal ends 8. The hole 5 is spaced apart from the open ends of the two channels 6 at the rear end of the carriage 4. While it is conceivable to employ more than two guide wires, it has been found that two wires normally suffice to hold the carriage 4 against turning in response to rotation of an electrode 1 or an analogous elongated slender object about its own axis.

Figure 8:
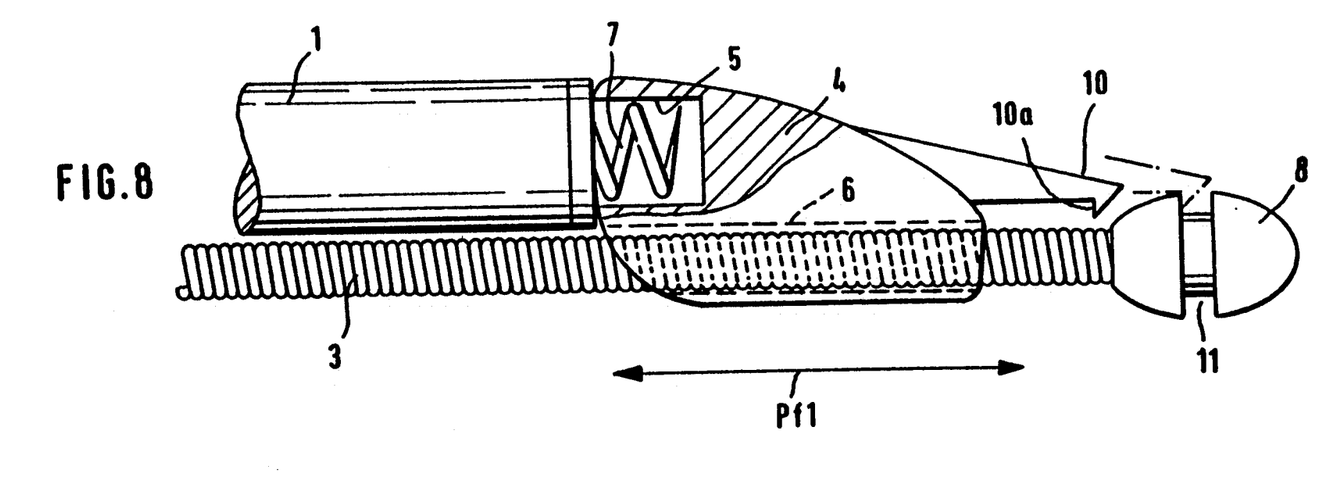
FIG. 8 is a fragmentary elevational view of an apparatus wherein the carriage and the distal end of the guide wire have detent elements which can hold the carriage in a selected position with reference to the distal end in order to facilitate separation of the leading end of an electrode from the carrier.

Another mode of ensuring that the carriage 4 cannot move in a direction away from the distal end of a single guide wire 3 or from the distal ends of two or more guide wires is shown in FIG. 8. The apparatus of FIG. 8 comprises means for holding the carriage 4 against movement in a direction away from the distal end 8 of the wire 3 with a force greater than that which is necessary to extract the helical leading end 7 of an electrode 1 from the blind hole 5 in the rear end of the carriage. To this end, the distal end 8 is provided with a female detent element 11 in the form of a circumferentially complete socket or groove, and the carriage 4 has a forwardly extending male detent element 10 in the form of a pawl with a pallet 10a which can snap into the socket 11 when the carriage advances into close or immediate proximity to the distal end 8. The operative position of the pallet 10a is shown in FIG. 8 by broken lines. The electrode 1 is then ready to be moved rearwardly (with reference to the carriage 4) in response to the application of a pull which is greater than the force tending to hold the helical leading end 7 of the electrode 1 in the hole 5. The apparatus of FIG. 8 renders it possible to extract the leading end 7 from the hole 5 without the need to rotate the electrode 1 about its axis, as long as the force with which the leading end 7 is held in the hole 5 is smaller than the force with which the pawl 10 holds the carriage 4 against movement away from the distal end 8 of the wire 3.

Figure 9:
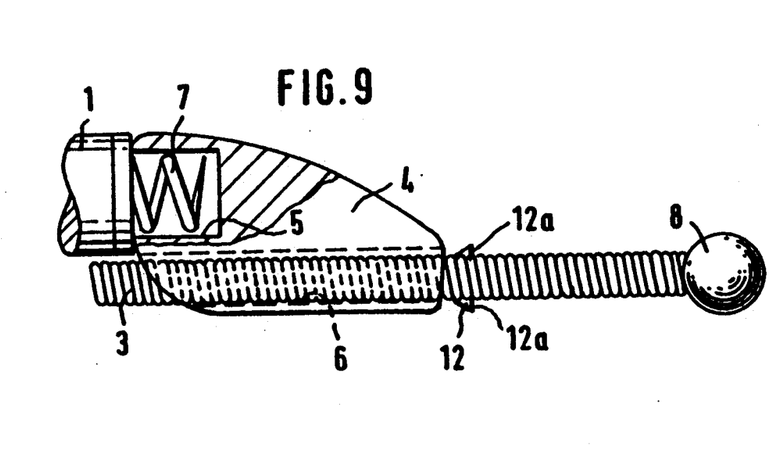
FIG. 9 is a fragmentary elevational view of an apparatus which constitutes a modification of the apparatus of FIG. 8 and employs different detent members, the carriage being shown in a position in which it is free to slide along the guide wire toward and away from the distal end.
Figure 10:
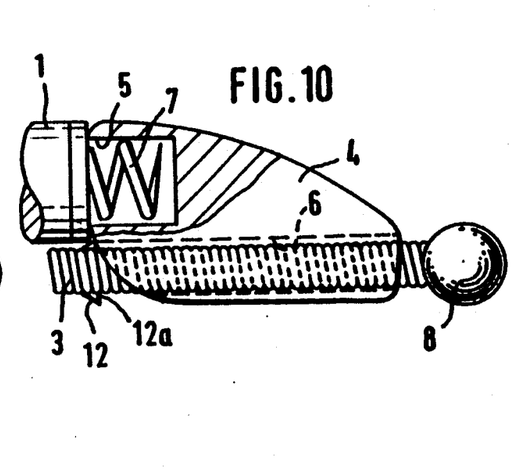
FIG. 10 shows the structure of FIG. 9 but with the carriage held by the guide wire at a predetermined distance from the distal end of the guide wire against movement away from the distal end.

FIGS. 9 and 10 show a portion of an apparatus which constitutes a modification of the apparatus of FIG. 8. The wire 3 carries an annular first detent element or stop 12 having a deformable shoulder 12a facing toward the distal end 8 of the wire. The surface at the open rear end of the channel 6 in the carriage 4 constitutes a complementary second detent element which can readily ride over the detent element 12 in a direction toward the distal end 8 but is arrested by the shoulder 12a when the carriage 4 tends to move away from the distal end (once the carriage has advanced beyond the detent element 12). The detent element 12 can be said to constitute a barb and is or can be at least slightly elastic so that it yields in response to engagement by the surface bounding the channel 6 while the carriage 4 advances toward the distal end 8 of the wire 3. The distance of the preferably ring-shaped shoulder 12a from the distal end 8 equals or exceeds the length of the carriage 4 (i.e., the length of the channel 6).

FIG. 9 shows the carriage 4 on its way toward the distal end 8, i.e., the detent element 12 is about to be deformed. FIG. 10 shows the carriage 4 in a position in which it is capable of moving toward but not in a direction away from the distal end 8 because the shoulder 12a of the detent element 12 abuts the surface at the rear end of the channel 6.

The detent elements 10 (FIG. 8) and 12 (FIGS. 9 and 10) can be made of a suitable plastic material which is preferably at least slightly elastic so that the pallet 10a can readily penetrate into the socket 11 and that the detent element 12 can readily expand in order to hold the carriage 4 against movement away from the distal end 8 of the respective wire 3.

Figure 11:
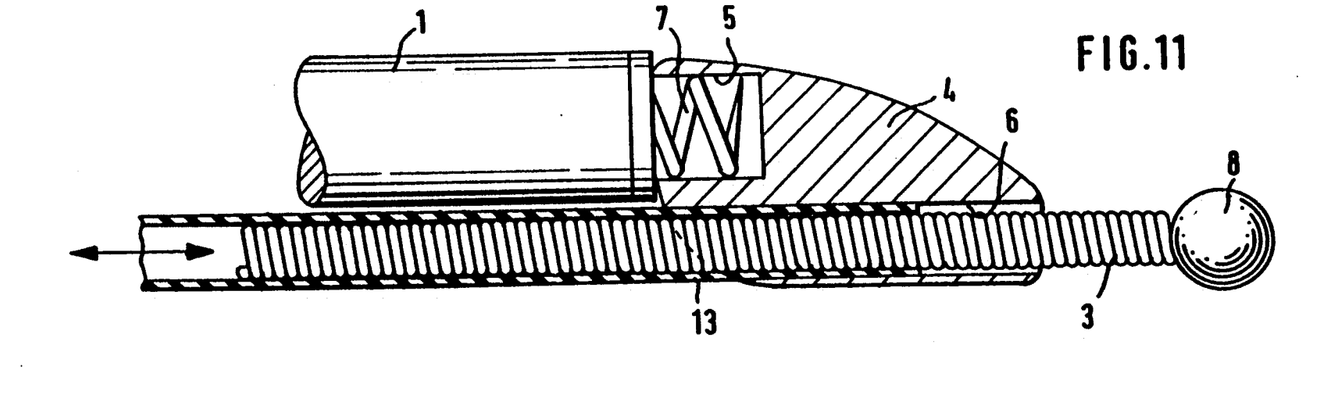
FIG. 11 is a fragmentary side elevational view of an apparatus wherein the carriage is held against movement away from the distal end of the wire by a tubular detent member which is slideable along the guide wire.

FIG. 11 shows a portion of a further apparatus wherein the means for preventing the carriage 4 from moving away from the distal end 8 of the wire 3 comprises a tubular stop or detent element 13 which surrounds the wire 3 beyond the channel 6. The front end of the detent element 13 can merely abut but is preferably affixed (e.g., bonded) to the carriage 4. This detent element 13 can constitute a length of flexible hose.

When the carriage 4 is pushed (by the detent element 13) to a position at an optimum distance from the distal end 8 of the wire 3, the element 13 is held against movement away from the distal end 8 to thus prevent retraction of the carriage 4 while the electrode 1 is pulled to the left to extricate the helical leading end 7 from the blind hole 5. It is also possible to rotate the electrode 1 in a direction to withdraw the leading end 7 from the carriage 4. Once the leading end 7 is extracted from the hole 5, the detent element 13 can be used to turn the carriage 4 about the wire 3 in order to move the rear end of the carriage out of the way and to thus enable the electrode 1 to move forwardly (e.g., toward and beyond the distal end 8 of the wire 3) in order to anchor the leading end 7 in the tissue of an animal body.

The detent element 13 can further serve as a means for moving the carriage 4 in a direction away from the distal end 8 of the wire 3. Thus, this detent element can perform a number of important function including moving the carriage 4 toward the distal end 8, holding the carriage against movement away from the distal end during extraction of the leading end 7 from the hole 5, turning the carriage about the wire 3, and moving the carriage away from the distal end.

Figure 12:
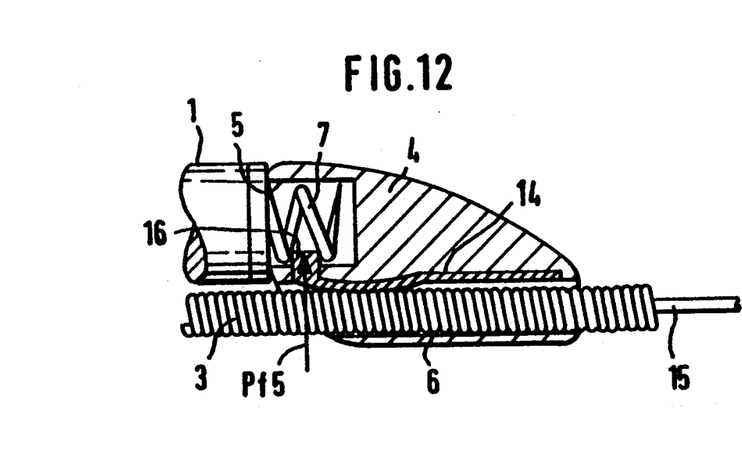
FIG. 12 is a fragmentary elevational view of an apparatus wherein the carriage can be held against movement away from the distal end of a modified guide wire by an elastic detent element in the form of a leaf spring and wherein the leaf spring also serves to releasably hold the leading end of an elongated object in the cavity of the carriage.
Figure 13:
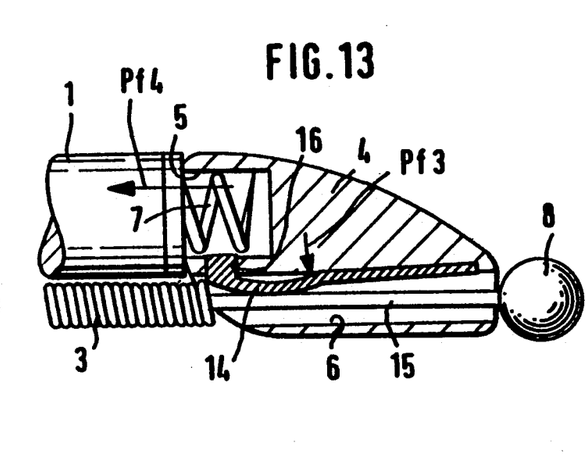
FIG. 13 shows the structure of FIG. 12 but with the leaf spring received in a recess of the guide wire and with the leaf spring disengaged from the leading end of the elongated object.

FIGS. 12 and 13 illustrate a further modification of the apparatus which is shown in FIGS. 9 and 10. The male detent element of this apparatus is an elongated leaf spring 14 which is installed in the carriage 4 in stressed condition so that its left-hand half tends to penetrate into the channel 6 but is normally prevented from entering the channel by the adjacent portion of the guide wire 3 (see FIG. 12). The wire 3 comprises a female detent element in the form of a recess 15 which is adjacent the distal end 8. Thus, when the leaf spring 14 reaches the position of FIG. 13, the left-hand half of the spring is free to move in the direction or arrow Pf3 and to enter the recess 15 so that the leaf spring then cooperates with the wire 3 to hold the carriage 4 against movement away from the distal end 8. This renders it possible to extract the leading end 7 of the electrode 1 from the blind hole 5 in the direction of arrow Pf4.

The leaf spring 14 can further serve as a means for preventing premature or untimely extraction of the leading end 7 of the electrode 1 from the blind hole 5 of the carriage 4. To this end, the left-hand end of the leaf spring 14 is provided with a projecting portion 16 which extends in a direction away from the channel 6 and enters the space between two neighboring helices or convolutions of the leading end 7 to thus block extraction of the leading end from the hole 5. The wire 3 urges the portion 16 in the direction of arrow Pf5 (FIG. 12) as long as the recess 15 is remote from the channel 6. Thus, while the projecting portion 16 permits introduction of the leading end 7 into the hole 5 by rotating the electrode 1 with reference to the carriage 4 and/or vice versa, the properly inserted leading end 7 cannot be simply extracted from the carriage 4 because two of its helices are held by the projecting portion 16 of the leaf spring 14. However, once the left-hand half of the leaf spring 14 is free to enter the recess 15, the projecting portion 16 is automatically expelled from the hole 5 and the leading end 7 can be readily withdrawn from the carriage in the direction of arrow Pf4. In fact, the leading end 7 need not be held in the hole 5 by friction so that it can be even more readily extracted from the carriage 4 as soon as the projecting portion 16 of the spring 14 assumes the inoperative position of FIG. 13.

If the element to be implanted is a catheter (such as the catheter 2 of FIG. 4), the front portion of the catheter can be provided with a radially extending socket for the projecting portion 16 of the leaf spring 14. Thus, the projecting portion 16 can penetrate between the convolutions or helices or a spiral leading end 7 or it can otherwise engage and releasably hold the leading end of an elongated object which is to be temporarily affixed to the carriage 4.

It will be noted that the male detent element (leaf spring) 14 of the apparatus which is shown in FIGS. 12 and 13 can perform two basically different functions, namely that of attaching the carriage 4 to the wire 3 at a predetermined distance from (e.g., in immediate or close proximity to) the distal end 8 of the wire, and that of preventing premature separation of the leading end of an electrode, catheter or another elongated slender object from the carriage 4.

Figure 14:
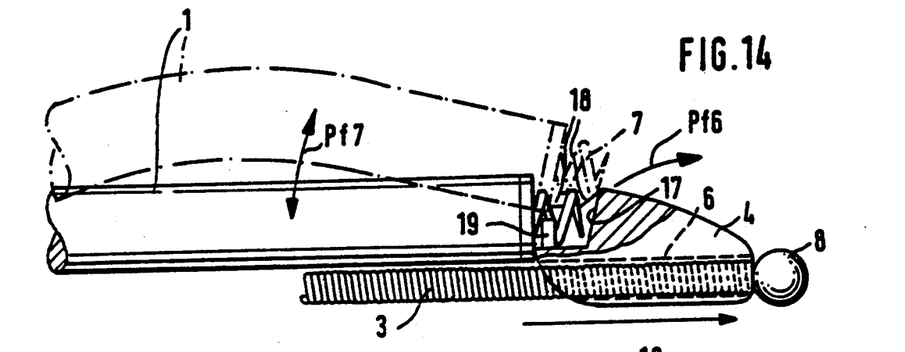
FIG. 14 is a fragmentary elevational view of an apparatus wherein an electrode or a catheter can be disengaged from the carriage by pushing it forwardly toward the distal end of the guide wire.
Figures 15, 16:
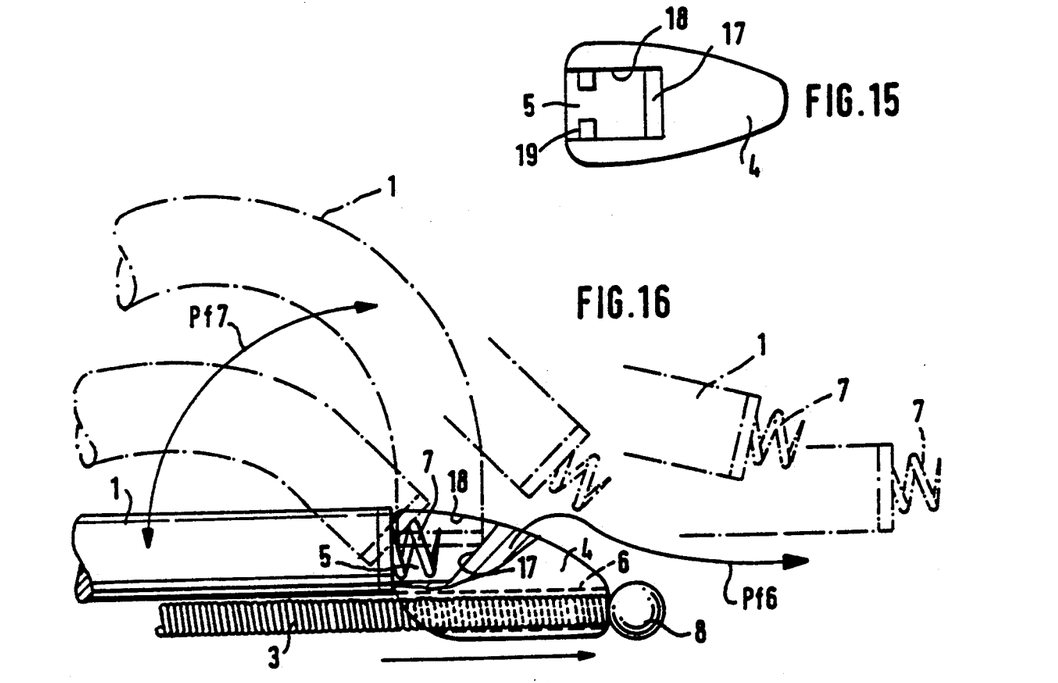
FIG. 15 is a plan view of the carriage which is used in the apparatus of FIG. 14.
FIG. 16 is a fragmentary elevational view of an apparatus which constitutes a modification of the apparatus of FIG. 14.

FIGS. 14 and 15 show a portion of an apparatus wherein the leading end 7 of an electrode 1 can be expelled from the carriage 4 to be simultaneously moved laterally of and away from the channel 6 for the guide wire 3 in response to the application of a force which urges the electrode forwardly, i.e., toward the distal end 8 of the wire. To this end, the inner or closed end of the cavity 5 in the rear end of the carriage 4 is adjacent a ramp 17 which slopes forwardly and outwardly in a direction away from the channel 6 and is adjacent a lateral outlet 18 of the cavity. When the electrode 1 is pushed forwardly, it tends to flex in the region behind its helical leading end 7 (as indicated by a double-headed arrow Pf7) and the tip of the leading end 7 slides along the inclined ramp 17 to enter into and to advance beyond the lateral outlet 18 of the carriage 4. The direction in which the tip of the leading end 7 of the electrode 1 advances along and thereupon forwardly beyond the ramp 17 is indicated by the arrow Pf6. As the electrode 1 tends to bend or actually bends from the solid-line position to the broken-line position of FIG. 14, it promotes the movement of the leading end 7 along the ramp 17 and toward and through the lateral outlet 18 of the carriage 4. The carriage 4 is held against forward movement under the action of the electrode 1 because its front end abuts the distal end 8 which cannot enter the channel 6. Thus, the apparatus of FIGS. 14 and 15 differs from the previously described apparatus (for example, from the apparatus of FIG. 8) in that the leading end of an object (such as the electrode 1) can be expelled from the cavity of the carriage 4 by urging the object and its leading end forwardly.

In order to prevent accidental (premature) separation of the leading end 7 of the electrode 1 of FIG. 14 from the carriage 4, for example, when the carriage is caused to advance along an arcuate path so that the leading end 7 would be likely to leave the cavity 5 via lateral outlet 18, the carriage 4 is preferably designed in a manner as shown in FIG. 15. Thus, the carriage is provided with at least one constriction 19 in the form of a clamp or the like having prongs which enter the spaces between the adjacent helices of the leading end 7. The force with which the clamp 19 holds the leading end 7 in the cavity 5 is overcome when the electrode 1 is forced forwardly so that the tip of the leading end 7 slides along and beyond the ramp 17.

Figure 17:
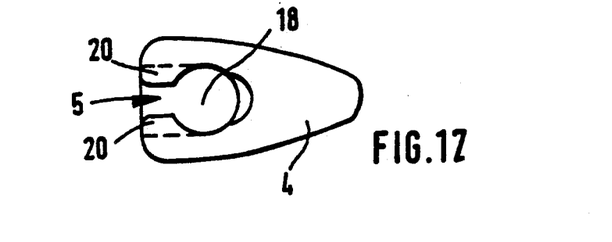
FIG. 17 is a plan view of the carriage which is used in the apparatus of FIG. 16.

FIGS. 16 and 17 show a portion of an apparatus which constitutes a modification of the apparatus of FIGS. 14 and 15. The constriction 20 of the carriage 4 extends also into the lateral outlet 18 of the carriage and narrows the outlet in a direction toward the rear end of the carriage. Thus, and as seen from the rear end toward the front end of the carriage 4, the lateral outlet 18 is narrower in the region of the two prongs of the constriction 20 and then widens adjacent the ramp 17. The larger portion of the outlet 18 permits the leading end 7 of an electrode 1 or the leading end of a catheter to pass therethrough in response to the application of a push which urges the leading end toward the ramp 17. The electrode 1 of FIG. 16 must be urged forwardly with a force which suffices to ensure that the orientation of the leading end 7 is changed through approximately 90° before such leading end can leave through the wide front portion of the lateral outlet 18. This is indicated in FIG. 16 by the arrow Pf7 which shows the direction of flexing or bending of the electrode 1 behind the leading end 7 for the purpose of enabling the latter to leave the cavity 5. Expulsion of the leading end 7 from the cavity 5 is somewhat similar to that which is shown in FIG. 2 except that, in FIG. 16, the leading end 7 of the electrode 1 changes its orientation with reference to the carriage 4. Deformation of the electrode 1 disappears or is reduced considerably as soon as the leading end 7 is expelled from the cavity 5. This is indicated in FIG. 16 by phantom lines showing the front portion of the electrode 1 in three different positions subsequent to expulsion of the leading end 7 from the cavity 5, i.e., while the leading end advances in the direction of arrow Pf6. The leading end 7 is thereupon anchored in (threaded into) the tissue in a selected portion of the body cavity (e.g., in cardiac tissue).

The apparatus which are shown in FIGS. 14 and 16 can be used with advantage for implantation of electrodes, catheters or like elongated objects as well as for highly predictable introduction of metered quantities of medicaments. For example, a capsule containing a dose of medicine can be injected into a selected portion of a human heart by expelling such capsule along the ramp 17 and through the outlet 18 as soon as the carriage 4 of FIG. 14 or 16 reaches a desired position in the heart. The means for expelling the cartridge via outlet 18 can constitute a mandrin or the like.

The improved apparatus can be used with advantage for implantation of an electrode into the ventricle of a heart or even into the auricle. The same holds true for the implantation of catheters. The carriage 4 not only ensures convenient implantation but also protects the tissue around a vein or the like from damage during introduction of an object. For example, the helical leading end 7 of an electrode 1 is properly confined in the cavity 5 during introduction of the electrode 1 so that the leading end cannot contact and eventually injure the adjacent tissue while the carriage slides toward the distal end or ends of the guide wire or wires 3.

If an electrode 1 with a helical leading end 7 is to be introduced into the right ventricle, it suffices to introduce the electrode close to the ventricle and to thereupon rotate the electrode in a direction to unwind the leading end 7 from the cavity 5 (e.g., in a manner as described with reference to FIG. 1). The thus extracted leading end 7 is thereupon anchored in a selected portion of the ventricle.

As mentioned above, the carriage 4 can be used to facilitate implantation of electrodes, catheters or other elongated slender objects as well as for controlled introduction of medications into selected portions of body cavities, e.g., into a human heart or into another hollow organ. This renders it possible to reduce the quantities of medicaments because the carriage 4 can deliver the required quantity of medication to the very locus where the medication is needed in a human or other animal body.

The carriage 4 can be provided with two or more discrete coupling means each of which is designed to properly engage a particular leading end (such as a helical leading end 7) or a different leading end. For example, one of the coupling means can have a blind hole or a through hole 5 for reception of a helical leading end 7, and another coupling means can have a hole 5a, 5b for reception of the leading end of a catheter 2.

The improved apparatus exhibits the advantages of heretofore known implanting apparatus but does not exhibit the drawbacks of such conventional apparatus. Thus, the apparatus of FIGS. 1 to 17 exhibits all advantages of apparatus which employ flexible guide wires, namely that the leading end of a catheter or an electrode can be led all the way to a selected part of a body cavity for anchoring in the tissue or for admission of medicaments. Moreover, the apparatus can be used for implantation of electrodes, catheters or other slender elongated objects which do not have or should not have specially designed leading ends for advancement along a guide wire. This is accomplished by the provision of a discrete carriage which has means for coupling it to the leading end of an electrode, a catheter or any other object which is to be implanted and wherein such coupling means can be designed to engage and releasably hold any existing leading end, be it a helical leading end or simply the front end portion of a tubular object (such as the catheter 2). The carriage 4 acts not unlike a shield or helmet in front of the leading end of the object which is to be implanted so that the tissue which is adjacent the path for implantation cannot be injured by the sharp tip of a helical leading end or by one or more sharp edges at the front end of a tubular object. The means for pushing the carriage along the guide wire or guide wires 3 can constitute an electrode, a catheter, a further guide wire or a mandrin, e.g., a mandrin which is received in the interior of a hollow electrode. If the carriage 4 is used as a vehicle for introduction of medicaments, it can be designed to transport medicaments in the form of capsules or the like, and such carriage can be pushed into an animal body with a mandrin or the like. For example, the carriage 4 can be used as a vehicle for available capsules which contain medicaments and automatically open or dissolve after elapse of a certain interval of time following introduction to be effective at the selected locus in the interior of an animal body. The locus of application or dissolution of introduced medicaments can be selected by the guide wire or wires 3 with a high degree of accuracy, and the carriage 4 is ready to transport one or more capsules to such locus as soon as the introduction of the guide wire or wires is completed. This renders it possible to avoid the introduction of excessive quantities of medicines because the entire dose is moved to the locus where the introduced medicine is to produce its beneficial effect, e.g., in a human heart.

It is also within the purview of the invention to design the carriage 4 in such a way that the axis of the cavity 5 forming part of the coupling means is inclined with reference to the axis or axes of one or more channels 6. However, the illustrated designs (wherein the axis of the blind hole 5, through hole 5 or composite hole 5a, 5b is parallel or at least nearly parallel to the axis or axes of one or more channels 6) are preferred at this time for the aforediscussed reasons. Thus, such carriage is much less likely to jam and to resist further movement along the guide wire or wires 3 in response to the application of a push to an electrode 1 or to a catheter 2. Moreover, such design ensures that the dimensions of the carriage 4 can be kept to a minimum because the combined space requirements of one or more cavities and one or more channels are minimal if the axes of such cavity or cavities and channel or channels are parallel to each other.

The catheter or catheters which are implantable with the improved apparatus can constitute flexible hoses.

A further important advantage of the improved apparatus is that it can pinpoint the locus of anchoring of the leading end of an electrode or the locus of positioning the open front end of a catheter with a very high degree of accuracy. This is due to the provision of the guide wire or wires 3 in conjunction with the carriage 4, and to the provision of coupling means which enables the carriage to steer the leading end of an object to be implanted or a capsule with medicine to a selected spot in a human heart or in another hollow body organ. Such ability of the improved apparatus is to introduce the carriage 4 (and hence the leading end of the object to be implanted or of a medicine-containing capsule) to a predetermined locus within an animal body exhibits another important advantage, namely that the interval of time which is required to complete an implantation or the admission of medicaments can be shortened to a fraction of the interval which elapses to complete an implantation or the admission of medicine with heretofore known apparatus. The reason is that the improved apparatus can ensure the advancement of its carriage 4 to an accurately selected location within an animal body on the first try, whereas a conventional apparatus invariably or normally carries out a series of attempts at proper positioning of the capsule with medicine or the leading end of a catheter or an electrode before the dispensing of medicine or the separation of the leading end from the guide wire can begin.

In addition, and as already pointed out above, the carriage 4 serves as a streamlined shield or helmet in front of the sharp leading end of a standard electrode or a mandrin so that the object to be implanted cannot damage the tissue adjacent the path for implantation of electrodes or the like. In other words, the apparatus can be used for implantation of electrodes which have desirable helical leading ends and are ready to be anchored in tissue as soon as the advancement of the leading end into a desired portion of the animal body is completed. This holds true even if the path along which the guide wire or wires 3 cause the carriage 4 to advance is an arcuate path with small radii of curvature in the bends.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. Apparatus for arterial or intravenous implantation of surgical electrodes, catheters and similar slender elongated objects having leading ends into the circulatory system or another cavity of an animal body, especially a human body, comprising at least one elongated flexible guide wire having a proximal end and a distal end; and a discrete carriage guided by and movable along said at least one wire toward and away from said distal end, said carriage having coupling means for releasably holding the leading end of a selected object so that the leading end which is held by said coupling means shares the movement of the carriage toward said distal end during implantation into the animal body and that the implanted leading end remains in the animal body upon separation from the coupling means and subsequent withdrawal of the coupling means and guide wire from the animal body.

2. The apparatus of claim 1, wherein said means includes a cavity provided in said carriage and arranged to receive the leading end of the selected object.

3. The apparatus of claim 1, wherein said carriage has an open-ended channel which receives said at least one guide wire.

4. The apparatus of claim 1 for implantation of electrodes having helical leading ends, wherein said coupling means includes a blind hole for the helical leading end of an electrode.

5. The apparatus of claim 1, wherein said carriage has a channel which receives said at least one guide wire, said channel having two open ends and one of said open ends being nearer to said distal end than the other of said open ends, the dimensions of said distal end being such that the distal end cannot enter the channel by way of said one open end.

6. The apparatus of claim 5, wherein said distal end has a substantially spherical shape.

7. The apparatus of claim 1, further comprising means for moving said carriage along said at least one guide wire.

8. The apparatus of claim 7, wherein said moving means includes means for moving said carriage in a direction away from said distal end.

9. The apparatus of claim 8, wherein said carriage includes a front end facing toward and a rear end facing away from the distal end of said at least one guide wire, said moving means including a cord which is connected to said carriage in the region of said rear end.

10. The apparatus of claim 1, wherein said carriage has a front end facing toward and a rear end facing away from said distal end, at least a portion of said carriage tapering in a direction from said rear end toward said front end.

11. The apparatus of claim 10, wherein said coupling means is provided in the region of the rear end of said carriage.

12. The apparatus of claim 1, wherein said carriage has a front end facing toward and a profiled rear end facing away from said distal end, said carriage further having an elongated channel which receives said at least one guide wire and said channel having a first open end in the region of the front end and a second open end in the region of the rear end of said carriage.

13. The apparatus of claim 12, wherein at least a portion of the rear end of said carriage is rounded.

14. The apparatus of claim 12, wherein at least a portion of the rear end of said carriage tapers in a direction away from said front end.

15. The apparatus of claim 12, wherein said rear end has a facet which makes an oblique angle with the axis of said channel.

16. The apparatus of claim 12, wherein said coupling means is disposed in the region of said rear end.

17. The apparatus of claim 1, wherein said carriage has an elongated channel which receives said at least one guide wire and said coupling means includes a cavity provided in said carriage and extending at least in part in substantial parallelism with said channel.

18. The apparatus of claim 1 for implanting objects having helical leading ends, wherein said coupling means includes an open-ended hole provided in said carriage and arranged to receive the helical leading end of a selected object and to permit penetration of the leading end through and beyond said hole for subsequent penetration into animal tissue.

19. The apparatus of claim 18, wherein said hole is tapped so that the helical leading end of a selected object can penetrate through and beyond said tapped hole as a result of rotation of the leading end with reference to said carriage.

20. The apparatus of claim 18, wherein said carriage includes means for clamping the leading end of a selected object in said hole.

21. The apparatus of claim 1, wherein said carriage has a front end facing toward and a rear end facing away from said distal end, said coupling means including a hole which has an open end in said rear end and extends toward the front end of said carriage, said hole including a first portion of smaller cross-sectional area nearer to said front end and a second portion of larger cross-sectional area nearer to said rear end.

22. The apparatus of claim 1, wherein said carriage has an open-ended channel which receives said at least one guide wire and said coupling means includes a hole in said carriage, said hole and said channel having circular cross-sectional outlines and being bounded by circumferentially complete cylindrical internal surfaces of said carriage.

23. The apparatus of claim 1, wherein said carriage has a first channel which receives said guide wire and said coupling means includes a second channel which receives the leading end of a selected object, said channels having identical cross-sectional outlines so that said first channel can receive the leading end of the selected object and said second channel can receive said at least one guide wire.

24. The apparatus of claim 1, wherein said carriage consists of a plastic material.

25. The apparatus of claim 1, wherein said carriage consists of a metallic material which is tolerated by a human body.

26. The apparatus of claim 25, wherein said metallic material is a high-quality steel.

27. The apparatus of claim 1, wherein said carriage has an open-ended channel which receives said at least one guide wire and a layer of inert plastic material, said carriage further having a surface surrounding said channel and said layer coating said surface.

28. The apparatus of claim 27, wherein said plastic material has a low coefficient of friction.

29. The apparatus of claim 1, further comprising means for preventing rotation of said carriage around said at least one guide wire.

30. The apparatus of claim 29, wherein said rotation preventing means includes a second guide wire, said carriage having a first open-ended channel which receives said at least one guide wire and a second open-ended channel which receives said second guide wire.

31. The apparatus of claim 30, wherein said coupling mean includes a cavity provided in said carriage and spaced apart from said channels.

32. The apparatus of claim 1, wherein said coupling means including means for releasably holding the leading end of a selected object with a first force, and further comprising means for attaching said carriage to a selected portion of said at least one guide wire with a greater second force so that, when said carriage is attached to said at least one guide wire, the leading end of the selected object can be separated from said carriage in response to exertion upon the selected object of a pull which exceeds said first force.

33. The apparatus of claim 32, wherein at least a portion of said attaching means is provided on said carriage.

34. The apparatus of claim 32, wherein at least a portion of said attaching means is provided on or in said at least one guide wire.

35. The apparatus of claim 32, wherein said attaching means comprises a first stop provided on said at least one guide wire and a second stop provided on said carriage and designed to ride over said first stop during movement of the carriage toward said distal end but to be held by said first stop against movement in a direction away from said distal end.

36. The apparatus of claim 32, wherein said attaching means comprises a first detent element provided on said carriage and a complementary second detent element provided on said distal end.

37. The apparatus of claim 36, wherein said second detent element comprises a socket in said distal end and said first detent element comprises a projection arranged to penetrate into said socket as said carriage approaches said distal end.

38. The apparatus of claim 36, wherein at least one of said detent elements consists of a plastic material.

39. The apparatus of claim 1, further comprising means for preventing movement of the carriage in a direction away from said distal end, including a tubular stop surrounding and slidable along said at least one guide wire to arrest said carriage at a selected distance of the carriage from said distal end.

40. The apparatus of claim 1, wherein said at least one guide wire has a recess adjacent said distal end and said carriage includes an elastic male detent element abutting said at least one guide wire and arranged to penetrate into said recess when said carriage reaches or approaches said distal end so that the detent element then cooperates with said at least one guide wire to prevent the carriage from moving away from said distal end.

41. The apparatus of claim 40, wherein said male detent element includes a leaf spring.

42. The apparatus of claim 40, wherein said carriage has an open-ended channel which receives said at least one guide wire and said detent element is installed in said carriage in stressed condition so that it tends to penetrate into said channel.

43. The apparatus of claim 40, wherein said coupling means includes a cavity provided in said carriage and arranged to receive the leading end of a selected object, said detent element having a portion which extends into said cavity to engage and hold the leading end of the selected object until said detent element is free to penetrate into said recess.

44. The apparatus of claim 43 for implantation of objects having helical leading ends, wherein said portion of said detent element is arranged to extend between the helices of the leading end in said cavity.

45. The apparatus of claim 43 for implantation of objects having sockets in the leading ends thereof, wherein said portion of said detent element is arranged to extend into the socket of the leading end in said cavity.

46. The apparatus of claim 1, wherein said coupling means includes a cavity for the leading end of a selected object and a ramp in front of said cavity, said carriage further having an outlet adjacent said ramp so that the leading end in said cavity can be expelled from the carriage by said ramp into and beyond said outlet in response to the application to a selected object of a force in a direction to urge the leading end of such object against said ramp.

47. The apparatus of claim 46, wherein said carriage has an open ended channel which receives said at least one guide wire and said outlet extends in a direction away from said channel.

48. The apparatus of claim 46 for implantation of objects having helical leading ends, wherein said cavity has an inlet for the leading end of a selected object and at least one constriction provided in the region of said inlet and having at least one portion arranged to penetrate between the helices of the leading end in said cavity.

49. The apparatus of claim 46, wherein said cavity has an inlet for the leading end of a selected object and said carriage includes a passage which communicates with and widens toward said outlet but is too narrow to permit escape of the leading end from said cavity.

* * * * *